(12) United States Patent
Funke et al.

(10) Patent No.: US 8,715,735 B2
(45) Date of Patent: May 6, 2014

(54) STABILISED SUPERSATURATED SOLIDS OF LIPOPHILIC DRUGS

(75) Inventors: Adrian Funke, Berlin (DE); Torsten Wagner, Berlin (DE); Ralph Lipp, Zionsville, IN (US)

(73) Assignee: Bayer Intellectual Property GmbH, Monehim (DE)

( * ) Notice: Subject to any disclaimer, the term of this patent is extended or adjusted under 35 U.S.C. 154(b) by 759 days.

(21) Appl. No.: 11/076,022

(22) Filed: Mar. 10, 2005

(65) Prior Publication Data
US 2005/0207990 A1    Sep. 22, 2005

Related U.S. Application Data

(60) Provisional application No. 60/551,330, filed on Mar. 10, 2004.

(51) Int. Cl.
| A61K 9/00 | (2006.01) |
| A61K 9/14 | (2006.01) |
| A61K 9/20 | (2006.01) |
| A61K 9/48 | (2006.01) |

(52) U.S. Cl.
USPC ............ 424/489; 424/400; 424/451; 424/464

(58) Field of Classification Search
USPC .................................. 424/464, 400, 451, 489
See application file for complete search history.

(56) References Cited

U.S. PATENT DOCUMENTS

| 4,013,785 | A | 3/1977 | Weintraub et al. | |
| 4,254,099 | A | 3/1981 | Asmussen et al. | |
| 4,639,370 | A | 1/1987 | Carli | |
| 5,569,652 | A | 10/1996 | Beier et al. | |
| 5,656,622 | A | 8/1997 | Bull et al. | |
| 5,789,442 | A | 8/1998 | Garfield et al. | |
| 6,027,747 | A | 2/2000 | Duclos et al. | |
| 6,787,531 | B1 * | 9/2004 | Hilman et al. | 514/171 |
| 2002/0142032 | A1 * | 10/2002 | Sherwood et al. | 424/465 |
| 2003/0054037 | A1 | 3/2003 | Babcock et al. | |
| 2003/0119798 | A1 * | 6/2003 | Heil et al. | 514/175 |
| 2006/0182691 | A1 | 8/2006 | Besse et al. | |

FOREIGN PATENT DOCUMENTS

| EP | 0336014 | 10/1989 |
| EP | 0474098 | 3/1992 |
| EP | 0492007 A1 * | 7/1992 |
| EP | 1 260 225 | 11/2002 |
| EP | 1 380 301 | 1/2004 |
| GB | 1365661 | 9/1974 |
| JP | 2006 505704 | 2/2006 |
| JP | 2006519820 | 8/2006 |
| KR | 10 2000 0016 | 3/2000 |
| WO | WO-97 47290 | 12/1997 |
| WO | WO 01/52857 | 7/2001 |
| WO | WO 0152857 | 7/2001 |
| WO | WO 03043630 | 5/2003 |
| WO | WO 2004/022065 | 3/2004 |
| WO | WO 2004/041289 | 5/2004 |
| WO | WO 2004/073689 | 9/2004 |
| WO | WO 2005/087194 | 9/2005 |

OTHER PUBLICATIONS

V. Buehler, "Kollidon (R). Polyvinylpyrrolidone for the pharmaceutical industry," Mar. 1998, BASF AG Fine Chemicals, Ludwigshafen, Germany, pp. 88-116, XP002297940.
K. Khougaz et al., "Crystallization inhibition in solid dispersions of MK-0591 and poly(vinylpyrrolidone) polymers," Journal of Pharmaceutical Sciences, Oct. 2000, vol. 89, No. 10, pp. 1325-1334, XP002297939, the whole document.
T. Watanabe et al., "Stability of amorphous indomethacin compounded with silica," International Journal of Pharmaceutics, 2001,vol. 226, pp. 81-91, XP002310637.
T. Watanabe et al., "Prediction of apparent equilibrium solubility of indomethacin compounded with silica by 13C solid state NMR," Int. J. Pharmaceutics, 2002, vol. 248, pp. 123-129, XP002310638.
T. Watanabe et al., "Comparison between polyvinylpyrrolidone and silica nanoparticles as carriers for indomethacin in a solid state dispersion," Int. J. Pharmaceutics, 2003, vol. 250, pp. 283-286, XP002310639.
H. Takeuchi et al., "Spherical solid dispersion containing amorphous tolbutamide embedded in enteric coating polymers or colloidal silica prepared by spray-drying technique," Chemical and Pharmaceutical Bulletin, Pharmaceutical Society of Japan, Tokyo, 1987, vol. 35, No. 9, pp. 3800-3806. XP001183548, ISSN: 0009-2363.
K.P.R. Chowdary et al., "Enhancement of dissolution rate of meloxicam," Indian Journal of Pharmaceutical Sciences, Mar. 2001, vol. 63, pp. 150-154, XP009037083, ISSN: 0250-474X.
H. Nakagami, "Solid dispersions of indomethacin and griseofulvin in non-porous fumed silicon dioxide, prepared by melting," Chemical and Pharmaceutical Bulletin, Pharmaceutical Society of Japan, Tokyo, Sep. 1991, vol. 39, No. 9, pp. 2417-2421, XP001183546, ISSN: 0009-2363.
D.C. Monkhouse et al., "Use of adsorbents in enhancement of drug dissolution I," Journal of Pharmaceutical Sciences, American Pharmaceutical Association, Washington, US, Sep. 1972, vol. 61, No. 9, pp. 1430-1435, XP001105645, ISSN: 0022-3549.
Degussa AG, Duesseldorf, "Aerosil (R)—Internet presentation—Entry No. 5—Dry binder: A new concept of pressed powders," 'Online! Retrieved from the internet: URL:https://www1.sivento.com/wps3/portal/action/ChangePage/.pg/85/.reqid/-1?cqurl=/en/aerosil/ebusiness/news0> retrieved on 12-114-2004 See "Aeroperl (R)".
Cab-O-Sil M5 © Product Inforamtion Sheet. Retrieved from http://talasonlinen.com/photos/inatructions/fumed_silica_info.pdf Published 2004.
Syloid 244 FP Silica Product Information Sheet. Retrieved from http://www.discoverysciences.com/uploadedFiles/Preparative_and_Process/B561_SYLOID_US_ver_FINAL.pdf Published 2011.
Limnel, Tarja. Mesoporous silica and silicon based materials as carriers for poorly water soluble drugs. Retrieved from https://helda.helsinki.fi/bitstream/handle/10138/27709/rnesoporo.pdf?sequence=1 published 2011.

* cited by examiner

*Primary Examiner* — Barbara P Badio
(74) *Attorney, Agent, or Firm* — Millen, White, Zelano, Branigan, P.C.

(57) ABSTRACT

Methods for improving solubility and bioavailability of lipophilic compounds are described. Particularly, described are stabilized supersaturated solid solutions, particularly in power from, of lipophilic drugs, such as steroidal molecules.

17 Claims, 2 Drawing Sheets

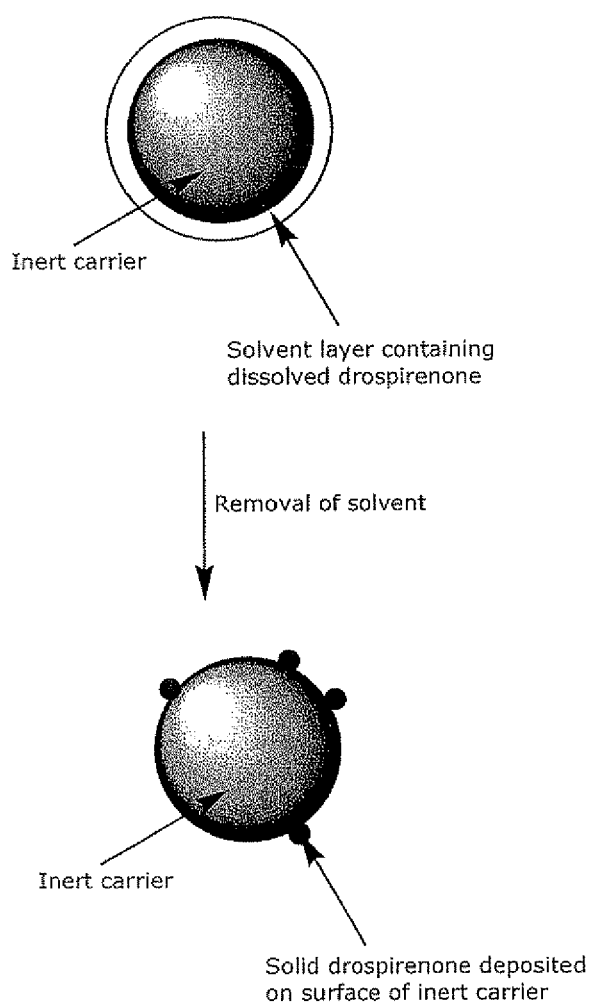

STABILISED SUPERSATURATED SOLIDS OF LIPOPHILIC DRUGS

Figure 1:
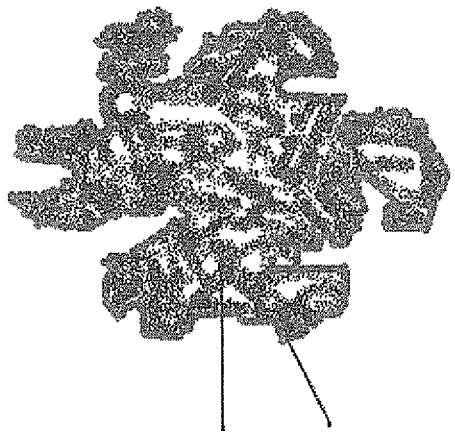

This application claims the benefit of the filing date of U.S. Provisional Application Ser. No. 60/551,330 filed Mar. 10, 2004.

FIELD OF INVENTION

The present invention relates to the field of pharmaceutical formulation science, in particular with respect to methods of improving solubility and bioavailability of lipophilic compounds. The specific formulation technique of the present invention relates to stabilised supersaturated solid solutions of lipophilic drugs, such as steroidal molecules and hormones in general. The solid solutions are suitable for being processed into tablets or other solid dosage forms.

BACKGROUND

Poor bioavailability of lipophilic compounds is a well-known problem, in particular in connection with per oral administration, wherein the compound is to be dissolved in the gastric fluid and/or intestinal fluid before being absorbed from the gastro-intestinal tract into the blood circulation. Thus, the rate-limiting step in the absorption of compounds from the gastro-intestinal tract is often the dissolution rate of the compound in water and other liquids, which are similar to the ones found in the gastro-intestinal tract.

Many attempts at increasing the solubility of a lipophilic compound have been suggested and used in the past years. Examples are attempts to increase the surface area of a compound, either by spraying the amorphous compound onto an inert carrier or by micronising the compound. Other attempts have been directed to inclusion complexes with cyclodextrins. A common feature of the conventional techniques is that the compound is in particulate form, eg. in amorphous form or in crystalline form. Both forms still require the initial step of dissolving the particulate compound before being capable of penetrating the mucosa of the gastro-intestinal tract.

Typical examples of pharmaceutical formulation techniques which result in particulate forms of lipophilic compounds in the final composition/dosage form rather than in molecularly dispersed lipophilic compounds are as follows:

EP 0474 098 relates to the formulation of solid compositions comprising a hardly soluble drug substance co-precipitated with a carrier comprising a water-soluble excipient (PVP) and a biodegradable excipient (polyactic acid). This formulation technique aims at solving the problem of providing controlled release formulations.

U.S. Pat. No. 4,639,370 relates to the formulation of powdery compositions comprising a poorly water-soluble drug in combination with a water insoluble carrier (cross-linked PVP). The compositions are prepared by grinding/milling the drug substance and the cross-linked PVP without dissolving the active drug.

WO 03/04360 relates to the formulation of solid dispersions comprising a poorly water-soluble drug in combination with a carrier (PVP). The compositions are prepared by dissolving the drug compound and the carrier (PVP) in a volatile solvent and then removing the solvent.

U.S. Pat. No. 6,027,747 relates to the formulation of solid compositions comprising a hardly soluble drug substance together with a carrier (PVP). The compositions are made by a process including dissolving the drug in a volatile organic solvent together with a hydrophilic polymer and evaporating the solvent to dryness to form a co-precipitate of the drug with the hydrophilic polymer.

Khougaz K et al. relates to the formulation of solid dispersions comprising a hardly soluble drug substance together with a carrier (PVP), wherein the drug substance is present in amorphous form or in crystalline form (Khougaz K et al. Crystallisation inhibition in solid dispersions of MK-0591 and PVP polymers, J Pharm Sci vol 89, October 2000, pages 1325-1334).

Watanabe T et al. relates to the formulation of solid compositions comprising indomethacin and silica. The indomethacin is physically mixed with the silica by co-grinding or melting resulting in amorphous form of indometacin (Watanabe T et al. Stability of amorphous indomethacin compounded with silica, Int J Pharm, 226, 2001, pages 81-91).

Watanabe T et al. also relates to the formulation of solid compositions comprising indomethacin and silica. The indomethacin is physically mixed with the silica by co-grinding or melting resulting in amorphous form of indometacin (Watanabe T et al. Prediction of apparent equilibrium solubility of indomethacin compounded with silica by 13C solid state NMR', Int J Pharm, 248, 2002, pages 123-129).

Watanabe T et al relates to the formulation of solid compositions comprising indomethacin and silica or PVP. The indomethacin is physically mixed with the silica or PVP by co-grinding or melting resulting in amorphous form of indometacin (Watanabe T et al. Comparision between Polyvinylpyrrolidone and silica nano particles as carriers for indomethacin in a solid state dispersion. Int J Pharm, 250, 2003, pages 283-286).

GB 1 365 661 relates to the formulation of solid compositions comprising a drug substance with low water solubility (Cholesteryl beta-glucoside) and a carrier (Silica (Aerosil™). The composition is prepared by dissolving the betaglucoside in hot ethanol and subsequently adding this solution to the aerosol powder and evaporate the solvent from the resulting slurry. The resulting composition has a slower release rate than conventional formulations.

Takeuchi et al relates to the formulation of compositions wherein the drug compound (tolbutamide) is present in amorphous form (Takeuchi et al. Spherical solid dispersion containing amorphous tolbutamide embedded in enteric coating polymers or colloidal silica prepared by spray-drying technique. Chem Pharm Bulletin Pharm Soc Japan. 35, 1987, pages 3800-3806).

Chowdary K et al. relates to the formulation of solid dispersions (powders) prepared by dissolving the drug (Meloxicam) in a solvent in the presence of carrier (Silica, Aerosil). The solvent is then evaporated to dryness. The process of evaporating the solvent to dryness will result in the drug precipitating onto the carrier (Chowdary K et al. Enhancement of dissolution rate of meloxicam. Indian J Pharm Sci, 63, 2001, pages 150-154).

Nakakami H relates to the formulation of solid dispersions comprising poorly water-soluble drugs and non-porous fumed silicon dioxide as the carrier (Nakakami H. Solid dispersions of indomethacin and griseofulvin in non-porous fumed silicon dioxide, prepared by melting. Chem Pharm Bulletin Pharm Sci Japan, 39, 1991, pages 2417-2421).

Monkhouse D C et al relates to the formulation of fine powders of a drug and a carrier (fumed silica). The drug and the silica are mechanically mixed under addition of an organic volatile solvent (acetone, chloroform or methylene chloride) in order to totally dissolve the drug in the sample. The solvent is then evaporated to dryness. As the solvent is evaporated to dryness the drug will precipitate onto the carrier (Monkhouse D C et al. Use of adsorbents in enhancement of drug dissolution I. J Pharm Sci, Am Pharm Ass Washington, 61, 1972, 1430-1435).

WO 01/52857 relates to the formulation of solid compositions comprising drospirenone and an estrogen, wherein the drospirenone is initially dissolved in a solvent and then sprayed onto the surface of an inert carrier.

Obviously, the administration of a compound that is in the dissolved stage already at the time of administration may be advantageous in terms of ensuring high bioavailability. For example, by dissolving a compound in a suitable oil or another lipophilic medium. Unfortunately, it is often found that the amount of drug which is dissolvable in the lipophilic media is too low, for which reason the oil cannot be administered in an acceptable form, such as enclosed in a capsule or the like.

Supersaturated solutions of lipophilic compounds are known approaches for making solutions containing lipophilic compounds in a dissolved stage. The concentration of a dissolved compound in a supersaturated solution is higher than the solubility of the compound in the actual solvent at room temperature. However, the physical stability of the compound in such a supersaturated solution is critical in that re-crystallisation of the compound occurs. Therefore, this technique cannot be applied as a general technique to lipophilic compounds as such.

Therefore, pharmaceutical dosage forms having the lipophilic drug in a readily dissolvable form and which are also physically stable (no tendency to crystallisation of the lipophilic drug) and which contain the lipophilic drug in a satisfactorily high concentration would solve the problems associated with other techniques.

SUMMARY OF INVENTION

The present inventors have found a formulation technique of stabilising supersaturated solutions of lipophilic drugs by adding a high surface amorphous silica to supersaturated solutions of a lipophilic drug compound so as to allow for the preparation of powdery compositions with a satisfactorily high concentration of a lipophilic drug. Furthermore, such a technique also results in physically stable compositions and an extremely fast dissolution rate. Beneficially, the thus formed powder can be processed directly into granulates or processed directly into tablets, in particular by direct tabletting.

Now provided is a composition in the form of a powder which comprises lipophilic compounds in molecularly dispersed form, a solvent or at least a residue of a solvent, and a carrier which has a specific surface area of at least 250 $m^2/g$. It is to be understood that the lipophilic compound is molecularly dispersed in the solvent or in the solvent that remains after evaporation.

Thus, in a first aspect, the invention relates to a powdery composition comprising a lipophilic molecule having a solubility in water at 25° C. lower than 1 mg/ml, such as a steroidal molecule; and a carrier, such as amorphous silica, having a specific surface area of at least 250 $m^2/g$; wherein the lipophilic molecule (such as a steroidal molecule) is molecularly dispersed in a solvent.

Compounds of the present invention are preferably steroidal molecules and hormones in general. In particular, drospirenone and estradiol valerate are preferred.

In a second aspect, the invention relates to a process for the preparation of a powdery composition of the invention, the process comprising the steps of a) dissolving in a solvent a lipophilic molecule having a solubility in water at 25° C. lower than 1 mg/ml, such as a steroidal molecule, in an amount that exceeds the saturation concentration of that steroidal molecule in the solvent; and b) mixing the resulting supersaturated solution of step a) with amorphous silica having a specific surface area of at least 250 $m^2/g$.

A further aspect of the invention relates to a process for the preparation of a powdery composition comprising a steroidal molecule molecularly dispersed in a solvent, where the amount of lipophilic component dissolved equals the saturation concentration of that lipophilic compound. In this aspect of the invention the process comprises the steps of a) dissolving in a solvent a steroidal molecule in an amount that is lower or equals the saturation concentration of that steroidal molecule in the solvent; and b) mixing the resulting saturated solution of step a) with amorphous silica having a specific surface area of at least 250 $m^2/g$; and c) evaporating off part of the solvent.

In a still further aspect, the invention relates to a pharmaceutical dosage form in the form of granules, a tablet, a capsule, or a pill, which comprises the powdery composition as defined herein.

In a still further aspect, the invention relates to the use of amorphous silica with a specific surface area greater than 250 $m^2/g$ for inhibiting the re-crystallisation of a compound that is present in a solvent in a supersaturated concentration.

DETAILED DESCRIPTION OF THE INVENTION

It has been found that lipophilic compounds can be provided in a highly water-soluble form using the technique of supersaturated solutions. First of all, the compound is completely dissolved in a suitable solvent by heating, if necessary, the liquid to high temperatures so as to achieve a supersaturated solution of the compound. Then, the solvent is adsorbed onto a solid carrier characterised by having a very high surface area. The resulting solid may be in the form of a powder, which comprises the compound completely dissolved and present in molecularly dispersed form within a thin film of the solvent that is adsorbed onto the large surface of the solid carrier. Advantageously, it has been discovered that the compound does not return into its crystalline form, even after long term storage and the resulting powder is applicable for being granulated or otherwise transferred into a suitable solid dosage form, such as being compressed directly into tablets. Advantageously, the dissolution rate is very high.

Thus, in a first aspect, the invention relates to a powdery composition comprising a steroidal molecule; and amorphous silica having a specific surface area of at least 250 $m^2/g$; wherein the steroidal molecule is molecularly dispersed in a solvent.

A particular aspect thereof relates to a composition in the form of a powder comprising drospirenone and amorphous silica having a specific surface area of at least 250 $m^2/g$, wherein the steroidal molecule is molecularly dispersed in a solvent.

Another particular aspect thereof relates to a composition in the form of a powder comprising estradiol valerate and amorphous silica having a specific surface area of at least 250 $m^2/g$, wherein the steroidal molecule is molecularly dispersed in a solvent.

As used herein, the term "molecularly dispersed" or "molecular dispersion" is used to describe any solid, semi-solid and liquid system in which the lipophilic compound is dispersed at the molecular level within or on a carrier. That is to say that the lipophilic drug is present in dissolved form in the solid phase. That is to say that the lipophilic drug is present in dissolved form in the solvent. The lipophilic compound cannot be detected in crystalline form, such as by X-ray diffraction, and the lipophilic compound is not detectable by microscopy, such as light microscopy or electron microscopy or by other relevant analysis of the molecular dispersion. That is to say that the lipophilic compound of the invention is neither present in a particulate form nor in a crystalline form. In fact, the lipophilic compound is present as distinct molecules and if examined under the electron microscope no particles are observed.

In practice "molecularly dispersed" compositions are formed by completely dissolving the lipophilic compound in a solvent. Some times the concentration of the lipophilic compound exceeds the amount that can be dissolved at room temperature. Subsequently, the solvent is mixed with a carrier resulting in the lipophilic compound being distributed evenly and homogenously onto the surface of the carrier at the molecular level. That is to say that the lipophilic compound is still present in dissolved form in the solvent absorbed onto the surface of the carrier. This phenomenon refers to the lipophilic compound being molecularly dispersed in the solvent/carrier.

The term "molecularly dispersed", when used herein, is meant to be interchangeable with the terms "molecular dispersion", "molecularly dissolved" and "molecular dissolution". In the present context the terms "molecularly dissolved" and "molecular dissolution" shall not be understood as a simple liquid solution as known in the art.

The term "saturated solution" is used to describe a solution containing a concentration of the lipophilic compound of the invention that is equal to the amount of compound that maximally can be dissolved at room temperature, the so-called "saturation concentration".

The term "supersaturated solution" is used to describe a solution containing a concentration of the lipophilic compound that is higher than its saturation concentration and wherein the full amount of the compound is still completely dissolved. Thus, even with the saturated concentrations of lipophilic compound no crystalline compound can be detected by powder X-ray diffraction analysis nor by other methods. Basically, supersaturated solutions are expected to be thermodynamically unstable leading to a saturated solution containing a recrystallized or precipitated (particulate) compound.

The term "stabilised supersaturated solution" is used to describe a supersaturated solution wherein neither a re-crystallized drug nor a precipitated (particulate) drug can be detected by powder X-ray diffraction analysis.

When applied to powder X-ray diffraction, absence of diffraction peaks corresponding to those of the crystalline drug indicates that the drug is present in a non-crystalline form such as a molecularly dispersed form.

As mentioned, Scanning Electron Microscopy may be used to detect whether the lipophilic drug is present in a molecularly dispersed form in that no particles may be observed in an electron microscope having a sensitivity below the "nano" size range.

A typical compound of the invention is characterised by being lipophilic and/or having a poor solubility in water at 25° C. In general, the compound has a solubility lower than 1 mg/ml in water at 25° C., such as lower than 0.5, 0.1, 0.05, or 0.01 mg/ml. Typically, the compound is an active pharmaceutical ingredient, such as a steroidal molecule and/or a hormone/anti-hormone in general. A large range of other active pharmaceutical ingredients may benefit from the present technology, such as albendazole, aminogluthethimide, aminosalicylic acids (3- 4- or 5-aminosalicylic acids) amiodarone, astemizole, azathioprine, beclamide, benorylate, benperidol, bezafibrate, biotin, bromocriptine, bromocriptine mesylate, bumetanide, busulphan, cabergoline, carbamazepine, cefixime, chenodeoxycholic acid, chlorambucil, chloroquine, chlorpropamide, chlorprothixene, chlorthalidone, cinnarizine, cinoxacin, clobazam, clofazimine, clofibrate, clonazepam, cyclopenthiazide, cyclosporin A, dapsone, demeclocycline, diazoxide, diflunisal, digitoxin, digoxin, disulfiram, domperidone, droperidol, enoxacin, epothilone, ethionamide, etretinate, felodipine, fenbufen, fexofenadine, flumazenil, folic acid, furosemide, glipizide, gliquidone, griseofulvin, haloperidol, hydrochlorothiazide, hydroflumethiazide, ibuprofen, iloprost, indomethacin, isocarboxazid, isosorbide dinitrate, isotretinoin, isradipine, itraconazole, ketazolam, ketoconazol, ketoprofen, lansoprazole, liothyronine sodium, lisuride, loperamide, loratadine, lorazepam, lovastatin, mebendazole, medazepam, mefenamic acid, menadione, mequitazine, methotrexate, misoprostol, morphine, niclosamide, nifedipine, nimodipine, nitrazepam, omeprazole, oxazepam, oxytetracycline, pantoprazole, perphenazine, phenylbutazone, pimozide, pindolol, probenecid, probucol, pyrantel embonate, pyrimethamine, retinol, riboflavin, simvastatin, stilboestrol, sulindac, sulphadiazine, sulphamethoxazole, sulphasalazine, sulpiride, tamoxifen, temazepam, thiabendazole, thioguanine, tocopherol, tolbutamide, tretinoin, triamteren, triazolam, trimethoprim and zopiclone.

As said, a compound of the invention is typically a steroidal molecule or otherwise a hormone of which can be mentioned:

androgens, such as testosterone and esters thereof (testosterone enanthate, testosterone undecanoate, testosterone cypionate, testosterone propionate)

estrogens/anti-estrogens, such as estradiol and esters thereof (estradiol valerate, estradiol enanthate, estradiol cypionate, estradiol undecylate), estriol, estrone, conjugated estrogens, equilin, ethinyl estradiol, fenestrel, mestranol, nylestriol, quinestrol, clomifene, estrogen receptor alpha agonists, estrogen receptor alpha antagonists, estrogen receptor beta agonists, estrogen receptor beta antagonists, estrogen receptor downregulators.

Corticosteroids, such as cortisones and glucocorticoids, e.g. beclomethasone dipropionate, betamethasone, betamethasone valerate, budesonide, clobetasol propionate, clobetasone butyrate, cortisone acetate, dexamethasone, fludrocortisone acetate, prednisolone, prednisone.

progestins/antiandrogens, such as cyproterone, drospirenone, etonogestrel, desogestrel, gestodene, levonorgestrel, norethisterones, norgestimate, norethindrone, norethindrone acetate, norethynodrel, norgestimate, norgestrel, medrogestone, medroxyprogesterone acetate, progesterone, progesterone receptor A specific ligands, progesterone receptor B specific ligands, mesoprogestins, antiprogestins, asoprisnil, asoprisnil ecamate.

Aldosterone antagonists, such as spironolactones, eplerenone, canrenoate, canrenone, dicirenone, mexrenoate, prorenoate, epostane, mespirenone, oxprenoate, spirorenone, spiroxasone, prorenone.

Vitamin D hormones, such as alfacalcidol, calcifediol, calciferol, calcitriol.

Thus, a steroidal molecule of the invention may be selected from estradiol and esters thereof, ethinyl estradiol, conjugated estrogens, testosterone and esters thereof, cyproterone, drospirenone, etonogestrel, desogestrel, gestodene, levonorgestrel, norethisterones, norgestimate, norethindrone, norethindrone acetate, norethynodrel, norgestimate, norgestrel, medrogestone, medroxyprogesterone acetate, progesterone, spironolactones, eplerenone, canrenoate, canrenone, dicirenone, mexrenoate, prorenoate, epostane, mespirenone, oxprenoate, spirorenone, spiroxasone, prorenone, asoprisnil, beclomethasone dipropionate, betamethasone, betamethasone valerate, budesonide, clobetasol propionate, clobetasone butyrate, cortisone acetate, dexamethasone, fludrocortisone acetate, prednisolone, prednisone, alfacalcidol, calcifediol, calciferol or calcitriol.

It is to be understood that the compositions of the invention may comprise more than one active drug substance, e.g. a combination of two ore more drug substances. For example, a composition of the invention may comprise a therapeutic effective dose of drospirenone and a therapeutic effective dose of an estrogen.

In currently interesting embodiments, the compound of the invention is estradiol valerate and/or drospirenone.

As said, the composition of the invention comprises a carrier, preferably a pharmaceutically acceptable carrier, which is characterised by having a high surface area. It has been found that the carrier should have a specific surface area greater than 200 m$^2$/g, preferably greater than 250 m$^2$/g. More preferably the carrier should have a specific surface area greater than 300 m$^2$/g. Obviously, the surface area may have an upper limit. It is generally acknowledged that the upper limit of the surface area is at the most 1000 m$^2$/g, such as at the most 800 m$^2$/g.

It has been found that such a carrier with a high specific surface area may be silica dioxide in amorphous form with a specific high surface area of about 300 m$^2$/g, such as the silica dioxide marketed under the name Aeroperl®. Aeroperl® is characterised by being an amorphous granulated fumed silica with a silicon dioxide content of over 99.8% w/w.

Silica dioxide is a well-known excipient usable for a broad range of purposes. It has been used as a crystallisation inhibitor in patch technology and as adsorber, anticaking and free flow agent, defoaming agent, drying agent (desiccant), filler, hydrophobizing agent for increasing water resistance, suspension stabiliser, gel-forming agent or viscosity adjuster.

Aeroperl® is able to absorb large amounts of oil and even then restore its good flowability properties. This renders the combination of Aeroperl® and an oil suitable for acting as a binder in the preparation of tablets. Due to the relatively large particle size of Aeroperl® the excipient has a lower dusting and is easier to handle in production.

The present inventors have found that amorphous silica dioxide, when applied in a form with high specific surface area, such as above 200 m$^2$/g, preferably above 300 m$^2$/g, more preferably above 350 m$^2$/g, stabilises the molecular dispersion of the compound in the composition. By example, crystals could not be detected by X-ray diffraction analyses in compositions of the invention. Thus, in other terms, the composition of the invention does not comprise crystals of the compound.

Alternative carriers with similar properties to silica dioxide may be applicable, for example polyvinylpyrrolidone (Povidone®, Kollidon®).

According to the invention, the compound is present in the composition in molecularly dispersed form. That is to say that the compound has been completely dissolved in a suitable solvent, which solvent is then adsorbed onto the solid carrier. Optionally, the solvent may be evaporated or otherwise reduced in an amount so that only sporadical amounts of the solvent remains in the composition. In the resulting composition it is to be understood that the compound is molecularly dispersed within the remaining solvent, which is adsorbed as a thin film onto the carrier, the high surface amorphous silica.

It is also to be understood that in the compositions of the invention the molecular dispersion of the compound is meant to define that the compound is in fact dissolved in the solvent, also after the solvent has been adsorbed by the carrier of the invention. In one embodiment of the invention, the compound is present in the solvent in a supersaturated concentration before the solvent is adsorbed onto the silica carrier material. The degree of super-saturation may vary. Typically the degree of super saturation is above 1.1, such as above 1.2. In general it is not possible to reach a degree of super-saturation greater than 2.5.

Further it must be understood that when measuring the dissolution rate of a composition according to the invention the dissolution rate is very fast. The fast dissolution rate is due to the fact that the molecularly dispersed compound is already present in a dissolved state and that once the composition has disintegrated, the release of the compound takes place immediately. The rate-determining step for the release is the disintegration time of the composition and not the dissolution step.

Suitable solvents for use in the dissolution of the lipophilic compound of the invention include but are not limited to: ethanol, isopropanol, glycerol, propylene glycol, transcutol, polyols, citric acid esters, monoglycerides, diglycerides, vegetable oils, partialsynthetic triglycerides e.g. medium chain triglycerides (MCT) such as miglyol®, synthetic triglycerides, mixtures of glycerol fatty acid esters such as Imwitor®, fatty alcohols, fatty alcohol ethers, fatty acids, fatty acid esters, waxes, paraffin, purified water or mixtures thereof.

Preferably, the solvent is selected from ethanol; propylene glycol; partial synthetic triglycerides; and vegetable oils. The vegetable oil is typically a mixture of fatty acid glycerides.

Typically, the vegetable oil is selected from olive oil; peanut oil and castor oil. Typically, olive oil complies with the quality described in Ph. Eur.; Olivae oleum raffinatum and/or the quality described in USPNF; Olive Oil. Typically, peanut oil complies with the quality described in Ph. Eur.; Arachidis oleum and/or the quality described in USPNF; Peanut oil. Typically, the castor oil complies with the quality described in Ph. Eur.; Ricini oleum virginale and/or the quality described in USP; Castor oil.

Typically, the partial synthetic triglyceride is a medium-chain triglyceride corresponding to the quality described in Ph. Eur.; Triglycerida saturate media. Suitable medium-chain triglycerides may also be known in the art as Bergabest®, Captex®, Crodamol®, Labrafac®, Myritol®, Neobee M5®, Nesatol®, Wagninol ® or Miglyol®. Preferably the medium-chain triglyceride is known in the art as Miglyol®, such as Miglyol® 810 or Miglyol® 812.

The ratio between the solvent and the carrier may be critical in terms of achieving a powder with good powder flowability and stability of the compound. Thus, in some embodiments the weighed ratio between the solvent and the carrier is ranging between 1:100 and 1:0.2, preferably between 1:50 and 1:0.5, more preferably between 1:20 and 1:0.5. Dependent on the type of solvent, the weighed ratio between the solvent and the carrier is normally in the range of 1:5 and 1:0.5, preferably about 1:2, 1:1 and 1:0.7.

The powdery compositions of the invention may in addition contain surfactants and co-solvents, which may be added to the above-mentioned solvents so as to modify the physicochemical properties of the solvent so as to increase the solubility of the lipophilic compound of the invention in the solvent.

Suitable surfactants include but are not limited to:
a) Lecithine
b) block copolymers of ethylene oxide and propylene oxide such as Pluronic® and Poloxamer® grades
c) glycerol esters, and polyoxyethylene glycerol esters, and mixtures thereof such as Gelucire® grades
d) sucrose fatty acid esters such as Sucroesters®
e) sorbitan fatty acid esters, and polyoxyethylene sorbitan fatty acid esters, and mixtures thereof such as Span® and Tween® grades
f) polyoxyethylene fatty acid esters, polyoxyethylene fatty alcohol ethers, and polyoxyethylene mono-, di- and triglyceride esters, and mixtures thereof, such as Cremophor® grades.

As said, the compositions of the invention are superior to those obtained by previously applied formulation techniques. In one embodiment, the invention provides compositions that exhibit one or more advantageous properties relative to an un-formulated compound.

For example, the in-vitro dissolution rate is high. It may be investigated in an in-vitro dissolution test method using 900-1000 mL of dissolution medium that ensures sink condition such as water or an aqueous solution of sodium dodecyl sulfate (37° C., 50-100 rpm) and a dissolution apparatus according to USP equipped with paddles. It was found that powdery composition of the invention exhibits fast dissolution of the compound in that more than 95% w/w of drospirenone was dissolved within the first 5 minutes of dissolution testing.

Thus, in a particular embodiment of the invention, the composition comprises as the compound drospirenone and at least 90% by weight of the drospirenone in the composition is dissolved within the first 5 minutes of in-vitro dissolution testing using as the dissolution medium 900-1000 mL of a medium ensuring sink condition, such as water or an aqueous solution of sodium dodecyl sulfate (0.4% sodium dodecyl sulfate) equilibrated at 37° C., and as the dissolution apparatus a USP apparatus equipped with paddles rotating with a speed of 50 or 100 rpm.

Generally, the composition of the invention includes the following superior properties, but is not limited to one or more of the following:
1. high bioavailability
2. low degradation of compound in gastric fluid or a fluid equivalent thereto
3. high absorption from the gastric mucosa
4. high in-vitro dissolution in dissolution media simulating the gastric fluid and/or intestinal fluid.
5. high in-vitro dissolution in water
6. improved blend uniformity
7. improved dose uniformity
8. improved flowability of the powdery composition
9. high load of compound in the compositions of the invention
10. high physically stability (no formation of precipitates/crystals) of the compound in the powdery composition so as to allow this powder to be stored for a long term As stated, the use of the high surface silica renders it possible to make stabilised solutions of lipophilic compounds dissolved completely at a concentration exceeding the saturation level of the compound in the solvent at room temperature (supersaturated solutions) and to transform this solution into a powdery composition without forming crystals or precipitates of the compound, even after long term storage.

Therefore, a particular aspect of the invention relates to the use of amorphous silica with a specific surface area greater than 250 $m^2/g$ for inhibiting re-crystallisation of a steroidal molecule that is present in a solvent in a supersaturated concentration.

It is an advantage of the present invention that it provides an active pharmaceutical ingredient in the form of a powder, which can be sieved, mixed with excipients, and encapsulated into hard gelatine capsules or directly compressed into tablets even without adding a binder.

Thus, in a further aspect, the invention relates to pharmaceutical dosage forms, which are in the form of granules, a tablet, a capsule, or a pill that comprises the powdery composition as defined herein.

The powdery compositions or the pharmaceutical dosage forms comprising the powdery compositions are preferably formulated in a manner allowing the compositions to be per orally administered. That is to say that in one embodiment of the invention, the composition of the invention is contacted with the gastric fluid following administration. In another embodiment, the compositions are formulated in a manner allowing the lipophilic compound or the compositions to pass the gastric fluid without being contacted with the gastric fluid, such as formulated with enteric coating material.

The composition comprising the molecular dispersion can, optionally, further comprise excipients selected from the group comprising disintegrants, lubricants, glidants, artificial sweeteners, bulking agents, colorants and one or more flavorants.

The composition comprising the molecular dispersion can be produced in solid dosage forms. Solid dosage forms include tablets, film coated tablets, granules, pellets, pills, capsules and powders including for example any modified release form of said dosage forms such as dosage forms with delayed release coatings, sustained release coatings, enteric coatings, immediate release formulations, effervescent dosage forms and chewable forms. Capsules include e.g. soft gelatine capsules, hard gelatine capsules, hydroxypropyl methyl cellulose (HPMC) capsules, and carragenane capsules.

In some embodiments, the powdery compositions may be suitably formulated for buccal or sublingual administration.

All dosage forms can be produced by methods well known in the art.

Typically, the amount of drug in the compositions of the prior art inventions ranges from about 1 to about 75 wt %, preferably from about 5 to about 50 wt %. When speaking about the final dosage form the amount of the compound ranges from about 0.1 to about 5.0 wt % in the pharmaceutical dosage form, such as tablets, granules, pellets or powders, preferably from about 1.0 to about 5.0 wt %. This is to say that typically the molecularly dispersed composition is present in the pharmaceutical dosage form in amounts ranging from about 5 and 100 wt %, preferably from about 10 and 50 wt %.

The composition of the invention may comprise a number of additional excipients.

Suitable disintegrants are selected from the group consisting of: croscarmellose sodium (a cross linked polymer of carboxymethylcellulose sodium), crospovidone, starch NF; polacrilin sodium or potassium and sodium starch glycolate. Those skilled in the art will appreciate that it is desirable for compressible tablets to disintegrate within 30 minutes, more desirable within 10 min, most desirable within 5 min; therefore, the disintegrant used preferably results in the disintegration of the tablet within 30 minutes, more preferable within 10 min, most preferable within 5 min.

Suitable lubricants include talc, magnesium stearate, calcium stearate, stearic acid, hydrogenated vegetable oils and the like. Preferably, magnesium stearate is used.

Suitable glidants include pyrogenic silica, talc and the like.

Suitable bulking agents include xylitol, mannitol, compressible sugars, lactose, calcium phosphate and microcrystalline celluloses.

Suitable artificial sweeteners include saccharin, cyclamates and aspartame.

If desired, known flavorants and known FD & C colorants can be added to the composition.

In a further aspect, the invention relates to the use of amorphous silica with a specific surface area greater than 250 m$^2$/g for inhibiting re-crystallisation of a compound that is present in a solvent in a supersaturated concentration.

Process for Preparing Molecular Dispersions of Lipophilic Drugs

Generally, super-saturated solutions can be prepared by dissolving a drug compound in a solvent in an amount exceeding the saturation concentration of the drug with respect to that solvent by means of heating, ultrasonic treatment, stirring and/or high speed mixing.

Without wishing to be limited to any specific mixing technology, stabilized supersaturated compositions of the invention can be prepared by mixing a supersaturated solution with the powdered carrier.

In case of using a volatile solvent, the compositions of the invention may be prepared by dissolving a drug compound in a solvent while not exceeding the saturation concentration of the drug with respect to that solvent and subsequently mix the resulting solution with the powdered carrier. By subsequent evaporation off a part of the solvent a supersaturated solid solution is formed.

Therefore, a further aspect of the invention relates to a process for the preparation of a powdery composition comprising a lipophilic compound of the invention, such as a steroidal molecule, molecularly dispersed in a solvent, the process comprising the steps of
   a) dissolving in a solvent a lipophilic compound (such as a steroidal molecule) in an amount that exceeds the saturation concentration of that lipophilic compound (such as a steroidal molecule) in the solvent; and
   b) mixing the resulting supersaturated solution of step a) with a carrier as defined herein, such as amorphous silica having a specific surface area of at least 250 m$^2$/g.

The process may optionally further comprise the step of reducing the amount of solvent, such as by evaporating off the solvent so as to achieve a thin film of solvent adsorbed onto the surface of the carrier.

A still further aspect of the invention relates to a process for the preparation of a powdery composition comprising a steroidal molecule molecularly dispersed in a solvent, where the amount of lipophilic component dissolved equals the saturation concentration of that lipophilic compound. In this aspect of the invention the process comprises the steps of
   a) dissolving in a solvent a steroidal molecule in an amount that is lower or equals the saturation concentration of that steroidal molecule in the solvent; and
   b) mixing the resulting saturated solution of step a) with amorphous silica having a specific surface area of at least 250 m$^2$/g; and
   c) evaporating off a part of the solvent.

The process may be applied to the lipophilic compounds defined herein, in particular applied with respect to steroidal molecules drospirenone and estradiol valerate. Likewise, any solvent, any carrier and any ratio between solvent and carrier as defined above may be applied in the process.

A preferred process for preparing stabilised supersaturated solutions of lipophilic drugs such as sex steroids is described in examples 1-4 and 6.

From example 6 it will be understood that various formulations according to examples 1 to 4 exhibit very fast in-vitro dissolution rates with respect to estradiol valerate and much faster than that of the micronised estradiol valerate ($D_{50}$<5 µm). Thus, in-vivo dissolution of the compositions of the invention will take place instantly as soon as the disintegration of the composition has taken place.

It was concluded that estradiol valerate is present in a molecularly dispersed form—that is to say—in an already dissolved form. Thus, the in-vitro dissolution test does not represent a dissolution procedure but rather reflects the disintegration time of the compound.

Example 7 shows the same result for drospirenone, and the above mentioned conclusion was verified by X-ray powder diffraction: no crystals could be found (example 8).

EXAMPLES

Example 1

When dissolving estradiol valerate in polyethylene glycol (PEG) 400 at room temperature, the saturation concentration was found to be approx. 50 g/L. A supersaturated solution of estradiol valerate is prepared by dissolving 91 g estradiol valerate in 1000 mL polyethylene glycol 400 by stirring at 55° C. The resulting liquid is mixed with 1000 g Aeroperl® 300 to give a powder with homogeneously absorbed liquid. 24 mg of the described stabilised supersaturated formulation contains 1 mg estradiol valerate.

Example 2

When dissolving estradiol valerate in peanut oil at room temperature, the saturation concentration was found to be approx. 30 g/L. A supersaturated solution of estradiol valerate is prepared by dissolving 39 g estradiol valerate in 1000 mL peanut oil by stirring at 55° C. The resulting liquid is mixed with 1667 g Aeroperl® 300 to give a powder with homogeneously absorbed liquid. 67 mg of the described stabilised supersaturated formulation contains 1 mg estradiol valerate.

Example 3

When dissolving estradiol valerate in medium chain triglycerides (MCT) at room temperature, the saturation concentration was found to be approx. 27 g/L. A supersaturated solution of estradiol valerate is prepared by dissolving 45 g estradiol valerate in 1000 mL medium chain triglycerides by stirring at 55° C. The resulting liquid is mixed with 1000 g Aeroperl® 300 to give a powder with homogeneously absorbed liquid. 44 mg of the described stabilised supersaturated formulation contains 1 mg estradiol valerate.

Example 4

A saturated solution of estradiol valerate is prepared by dissolving 89 g estradiol valerate in 1000 mL ethanol by stirring at room temperature. The resulting solution is mixed with 1000 g Aeroperl® 300 giving a dry powder by partly ethanol evaporation. 16 mg of the described stabilized supersaturated formulation contains 1 mg estradiol valerate.

Example 5

Formulations according to the examples 1 to 4 were investigated in an in-vitro dissolution test according to USP XXVIII Paddle apparatus 2 using 1000 mL of an 0.4% aqueous solution of sodium dodecyl sulfate as dissolution medium to ensure sink condition (37° C., 75 rpm). The amount of formulations to be tested was selected so that the composition contains approx. 1 mg of estradiol valerate. As reference, 1 mg unformulated estradiol valerate was investigated.

| Formulation | Release estradiol valerate [mg] | | | | |
| --- | --- | --- | --- | --- | --- |
| | 3 min | 6 min | 10 min | 15 min | 30 min |
| Estradiol valerate (micronised) | 0.34 | 0.41 | 0.47 | 0.67 | 0.76 |
| Formulation according to example 1 (PEG 400) | 0.50 | 0.52 | 0.58 | 0.63 | 0.68 |
| Formulation according to example 2 (peanut oil) | 0.72 | 0.75 | 0.78 | 0.79 | 0.80 |
| Formulation according to example 3 (MCT) | 0.86 | 0.90 | 0.91 | 0.97 | 0.99 |
| Formulation according to example 4 (ethanol) | 0.92 | 0.88 | 0.88 | 0.89 | 0.90 |

Example 6

A saturated solution of drospirenone is prepared by dissolving 17.56 g drospirenone in 1000 mL ethanol by stirring at room temperature. The resulting solution is mixed with 1000 g Aeroperl® 300 giving a dry powder by partly ethanol evaporation. 61 mg of the described stabilised supersaturated formulation contains 1 mg drospirenone.

Example 7

57 mg of the formulation according to the example 6 was investigated in an in-vitro dissolution test using 900 mL of water (37° C., 50 rpm). The following results were found: Drospirenone released after 5 min: 97.1%, after 10 min: 99.9%, after 15 min: 100.3%, and after 30 min: 100.6%.

Example 8

The formulation according to example 6 was investigated by X-ray powder diffraction (XRPD). Crystals could not be detected.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of U.S. Provisional Application Ser. No. 60/551,330, filed Mar. 10, 2004, is incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A powdery pharmaceutical composition comprising
a steroidal molecule;
a pharmaceutically acceptable amorphous silica carrier having a specific surface area of greater than 200 $m^2/g$; and
a pharmaceutically acceptable solvent
said solvent being present on the surface of said pharmaceutically acceptable carrier and said solvent comprising an amount of the steroidal molecule sufficient to provide a supersaturated concentration thereof
wherein said powdery pharmaceutical composition is prepared by
a) dissolving said steroidal molecule in said solvent in an amount that equals the saturation concentration of the steroidal molecule, mixing the resulting saturated solution with said pharmaceutically acceptable carrier and evaporating off a part of the solvent so as to provide a supersaturated concentration thereof
or
b) dissolving said steroidal molecule in said solvent in an amount that exceeds the saturation concentration of the steroidal molecule
and mixing the resulting saturated solution with said pharmaceutically acceptable carrier so as to provide a supersaturated concentration thereof.

2. The composition according to claim 1, wherein the steroidal molecule is estradiol or an ester thereof, ethinyl estradiol, a conjugated estrogen, testosterone or an ester thereof, cyproterone, drospirenone, etonogestrel, desogestrel, gestodene, levonorgestrel, norethisterones, norgestimate, norethindrone, norethindrone acetate, norethynodrel, norgestimate, norgestrel, medrogestone, medroxyprogesterone acetate, progesterone, spironolactones, eplerenone, canrenoate, canrenone, dicirenone, mexrenoate, prorenoate, epostane, mespirenone, oxprenoate, spirorenone, spiroxasone, prorenone, asoprisnil, beclomethasone dipropionate, betamethasone, betamethasone valerate, budesonide, clobetasol propionate, clobetasone butyrate, cortisone acetate, dexamethasone, fludrocortisone acetate, prednisolone, prednisone, alfacalcidol, calcifediol, calciferol or calcitriol.

3. The composition according to claim 2, wherein the steroidal molecule is drospirenone and/or estradiol valerate.

4. The composition according to claim 1, wherein the steroidal molecule is drospirenone.

5. The composition according to claim 1, wherein the solvent is ethanol, partial synthetic triglyceridel, or a vegetable oil.

6. The composition according to claim 1, wherein the specific surface area of said pharmaceutically acceptable carrier is at least 250 $m^2/g$.

7. The composition according to claim 6, wherein the specific surface area of said pharmaceutically acceptable carrier is at least 300 $m^2/g$.

8. A powdery pharmaceutical composition according to claim 1, wherein part of said solvent is evaporating off after mixing.

9. A pharmaceutical dosage form in the form of granules, a tablet, a capsule, or a pill comprising the composition as defined in claim 1.

10. A process for the preparation of a powdery composition comprising a steroidal molecule according to claim 1, the process comprising
a) dissolving completely in a solvent a steroidal molecule in an amount that exceeds the saturation concentration of the steroidal molecule in the solvent; and b) mixing the resulting supersaturated solution of step a) with a pharmaceutically acceptable carrier having a specific surface area of at least 200 m$^2$/g.

11. A process for the preparation of a powdery composition comprising a steroidal molecule according to claim 1, the process comprising
   a) dissolving completely in a solvent a steroidal molecule in an amount that equals the saturation concentration of the steroidal molecule in the solvent; and
   b) mixing the resulting saturated solution of step a) with a pharmaceutically acceptable carrier having a specific surface area of at least 200 m$^2$/g; and
   c) evaporating off a part of the solvent.

12. The process according to claim 10, wherein the steroidal molecule is estradiol or an ester thereof, ethinyl estradiol, a conjugated estrogen, testosterone or an ester thereof, cyproterone, drospirenone, etonogestrel, desogestrel, gestodene, levonorgestrel, norethisterones, norgestimate, norethindrone, norethindrone acetate, norethynodrel, norgestimate, norgestrel, medrogestone, medroxyprogesterone acetate, progesterone, spironolactones, eplerenone, canrenoate, canrenone, dicirenone, mexrenoate, prorenoate, epostane, mespirenone, oxprenoate, spirorenone, spiroxasone, prorenone, asoprisnil, beclomethasone dipropionate, betamethasone, betamethasone valerate, budesonide, clobetasol propionate, clobetasone butyrate, cortisone acetate, dexamethasone, fludrocortisone acetate, prednisolone, prednisone, alfacalcidol, calcifediol, calciferol or calcitriol.

13. The process according to claim 10, wherein the steroidal molecule is drospirenone and/or estradiol valerate.

14. The process according to claim 10, wherein the solvent is ethanol, partial synthetic triglyceride, or a vegetable oil.

15. The process according to claim 10, further comprising evaporating off the solvent.

16. A powdery composition obtained by the process of claim 10.

17. A process for preparing a tablet comprising a steroidal molecule and a pharmaceutically acceptable carrier having a specific surface area of greater than 200 m$^2$/g
   comprising:
   a) preparing a powdery composition according to claim 1; and
   c) directly compressing said composition into a tablet.

* * * * *